Feb. 7, 1961 A. C. SODANO Plant Pat. 2,022
ROSE PLANT
Filed April 4, 1960
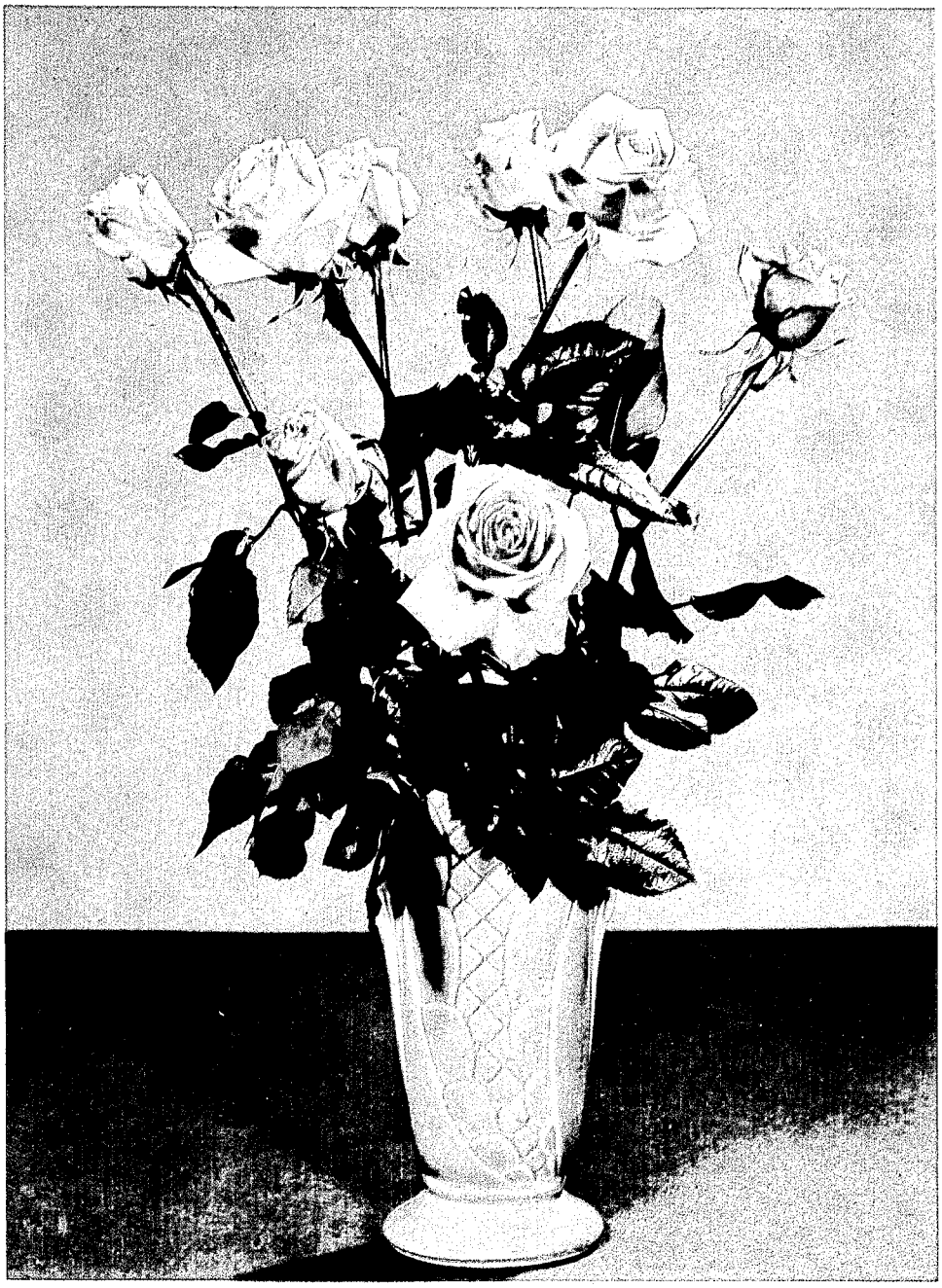
INVENTOR
Alfonso C. Sodano
BY Robb & Robb
ATTORNEYS United States Patent Office Plant Pat. 2,022
Patented Feb. 7, 1961

2,022

ROSE PLANT

Alfonso C. Sodano, Newtown, Pa., assignor to A. Sodano & Son, Newtown, Pa., a partnership Filed Apr. 4, 1960, Ser. No. 19,974

1 Claim. (Cl. 47—61)

The present invention relates to a new and distinct variety of rose plant of the floribunda class, which was discovered by me as a sport of the variety known as "Elfe" (unpatented).

This new sport was discovered by me while grading plants of the parent variety "Elfe" which were being grown in my greenhouses located at Newtown, Bucks County, Pennsylvania. During the course of my grading work, my attention was attracted to a plant in which both the flowers and the habits of the plant were substantially different from those of the parent variety "Elfe." Upon closer examination of this plant, I found that it had sported, and I thereupon took steps to carefully preserve the sport, keep it under observation, and to later asexually reproduce the same. These observations and asexual reproductions, as performed by both budding and grafting in my greenhouses at Newtown, Bucks County, Pennsylvania, conclusively established the existence of important differences between the sport and the variety "Elfe," and that these differences were fixed and established, as well as capable of being transmitted through succeeding propagations.

Among the outstanding characteristics of the new variety, the following features contribute to the novelty and distinctiveness thereof, and represent a unique combination which is definitely different from that found in the parent variety, or in any other variety of which I am aware:

(1) Foliage which is darker and glossier than that of the variety "Elfe," and which is comparable in color to the foliage of English holly, with the foliage being borne closer together on the stems than is customary with any other rose variety with which I am familiar;

(2) A larger flower size and greater flower petalage than is normally found in the parent variety "Elfe," with the flowers borne on stems having a shorter neck and greater rigidity;

(3) A more uniform texture of the flowers;

(4) A distinctive deeper pink general color tonality of the flowers;

(5) A more outstanding and pleasing flower fragrance; and (6) Good keeping qualities of the flowers when cut.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Sport of "Elfe."

Classification:

*Botanic.*—Floribunda.

*Commercial.*—Floribunda.

Propagation: Holds its distinguishing characteristics through succeeding propagations by both budding and grafting.

*Flower*

(Observations made from specimens grown in a greenhouse at Newtown, Bucks County, Pennsylvania, in the early afternoon during the latter part of the month of November.)

Blooming habit: Recurrent—continuous.

Bud:

*Size.*—Medium.

*Form.*—Ovoid; is not affected by wet or hot weather.

*Color.*—When sepals first divide—Spinel Red, Plate 26. When pedals begin to unfurl—Rosolane Purple, Plate 26, lightly overcast with Spinel Red, Plate 26. When half-blown: inside of petals—Rose color, Plate 12, with lower half of petals lightly overcast with Spinel Pink, Plate 26; reverse of petals—Rose color, Plate 12.

*Sepals.*—Branched; curl back when petals begin to unfurl. Color: inside—Turtle Green, Plate 32; outside—Biscay Green, Plate 17.

*Calyx.*—Color—Oil Green, Plate 5. Shape—funnel. Size — small. Aspect — smooth. Odor when rubbed—none.

*Peduncle.* — Length — medium. Aspect — prickly. Strength—erect; heavy. Color—Light Cress Green, Plate 31.

*Opening.*—Opens up well.

Bloom:

*Size.*—Large. Average size when fully expanded—from 3½ inches to 4 inches.

*Borne.*—Both singly and several together.

*Stems.*—Medium length; strong.

*Form (when first open).*—Cupped. Permanence—retains its form to the end.

*Petalage.*—Double. Number of petals under normal conditions—from 50 to 55.

*Color.*—Center of flower—Deep Rose Pink, Plate 12. Outer petals—Thulite Pink, Plate 26, with outer edges of petals lightly overcast with Deep Rose Pink, Plate 12. Base of petals (aiglet)—Light Cadmium, Plate 4. Inside of petals—Deep Rose Pink, Plate 12, lightly overcast with Thulite Pink, Plate 26. Reverse of petals—Pale Rosolane Purple, Plate 26, lightly overcast with Deep Rose Pink, Plate 12. General tonality from a distance—Deep Rose Pink, Plate 12.

*Discoloration.*—General tonality at end of first day—Deep Rose Pink, Plate 12. Second day—Deep Rose Pink, Plate 12, lightly overcast with Thulite Pink, Plate 26. Third day—Thulite Pink, Plate 26.

Petals:

*Texture.*—Leathery; is not affected by wet or hot weather.

*Appearance.*—Inside—satiny. Outside—shiny.

*Form.*—Oval.

*Arrangement.* — Imbricated (regularly arranged shingle-like).

*Persistence.*—Drop off cleanly.

*Petaloids in center.*—Few; small.

*Fragrance.*—Strong. Nature—fruity (russet apple).

*Lasting quality.*—On the plant—very long. As cut flower—very long.

*Genital organs*

Stamens, anthers: Medium size; many; regularly arranged around styles. Color—Yellow Ocher, Plate 15.

Stamens, filaments (threads): Medium length. Color—Orange Pink, Plate 2.

Pollen: Color—Light Buff, Plate 15.

Styles: Bunched; even length; medium length; thin.

Stigmas: Color—Martius Yellow, Plate 4.

Ovaries: All enclosed in calyx.

Hips: None.
Seeds: None.

*Plant*

Form: Bush.
Growth: Vigorous; upright.
Foliage: Compound of 3 to 5 leaflets.
*Size.*—Large.
*Quantity.*—Normal.
*Color.*—New foliage: upper side—Lettuce Green, Plate 5, with serrations Oxblood Red, Plate 1; under side—Lettuce Green, Plate 5, lightly overcast with Oxblood Red, Plate 1. Old foliage: upper side—Dark Cress Green, Plate 31; under side—Bice Green, Plate 17.
*Shape.*—Oval pointed.
*Texture.*—Upper side—leathery and glossy. Under side—smooth.
*Ribs and veins.*—Ordinary.
*Edge.*—Serrated (saw-toothed).
*Serration.*—Both double and single; small.
*Leaf stem.*—Color—Biscay Green, Plate 17. Under side—prickly.
*Stipules.*—Medium length; smooth.
Wood:
*New wood.* — Color — Courge Green, Plate 17. Bark—smooth.
*Old wood.* — Color — Spinach Green, Plate 5. Bark—smooth.

Thorns:
*Thorns.*—Quantity: on main stalks from base—ordinary; on laterals from stalk—ordinary. Form—narrow base; medium length; hooked downward. Color (when young)—Eugenia Red, Plate 13. Position—irregular.
*Prickles.*—Quantity: on main stalks—none; on laterals—none.
*Short needles.*—Quantity: on main stalks—none; on laterals—none.

I claim:

A new and distinct variety of rose plant of the floribunda class, substantially as herein shown and described, characterized particularly as to novelty by the unique combination of foliage which is glossier and darker than the foliage of the variety "Elfe" (unpatented) and comparable in color to the foliage of English holly, said foliage being borne relatively close together on the stems, a larger flower size and greater petalage than the flowers of the variety "Elfe," with the flowers borne on stems having a shorter neck and greater rigidity, a more uniform texture of the flowers, a distinctive deeper pink general color tonality of the flowers, a more outstanding flower fragrance, and good keeping qualities of the flowers when cut.

No references cited.